United States Patent [19]

Ehlhardt et al.

[11] Patent Number: 5,262,440
[45] Date of Patent: Nov. 16, 1993

[54] ANTITUMOR COMPOSITIONS AND METHODS OF TREATMENT

[75] Inventors: William J. Ehlhardt; James E. Ray; John E. Toth, all of Indianapolis, Ind.

[73] Assignee: Eli Lilly and Company, Indianapolis, Ind.

[21] Appl. No.: 805,417

[22] Filed: Dec. 10, 1991

[51] Int. Cl.$^5$ .................. A61K 31/175; C07C 311/60
[52] U.S. Cl. ...................................... 514/392; 564/39
[58] Field of Search ........................ 564/39; 514/592

[56] References Cited

U.S. PATENT DOCUMENTS

| | | | |
|---|---|---|---|
| 3,083,207 | 3/1963 | Hoehn et al. | 260/319 |
| 3,097,242 | 7/1963 | Hoehn et al. | 260/553 |
| 3,102,115 | 8/1963 | Breuer et al. | 260/239 |
| 3,102,121 | 8/1963 | Breuer et al. | 260/330.5 |
| 3,736,122 | 5/1973 | Tung et al. | 71/103 |
| 3,849,110 | 11/1974 | Soper et al. | 71/103 |
| 4,845,128 | 7/1989 | Harper et al. | 514/592 |

FOREIGN PATENT DOCUMENTS

| | | |
|---|---|---|
| 1208561 | 7/1986 | Canada . |
| 107214 | 9/1983 | European Pat. Off. . |
| 166615 | 1/1986 | European Pat. Off. . |
| 222475 | 5/1987 | European Pat. Off. . |
| 291269 | 11/1988 | European Pat. Off. . |
| 1240866 | 6/1961 | Fed. Rep. of Germany . |
| 1144259 | 2/1963 | Fed. Rep. of Germany . |
| 1159937 | 12/1963 | Fed. Rep. of Germany . |

OTHER PUBLICATIONS

W. J. Ehlhardt, *Drug Metabolism and Disposition*, 19:370 (1991).
J. J. Howbert, et al., *Synthetic Communications*, 20:3193 (1990).
W. J. Ehlhardt, *Drug Metabolism and Disposition*, 19:366 (1991).
J. J. Howbert, et al., *Journal of Medicinal Chemistry*, 33:2393 (1990).
G. B. Grindey, et al., *Proceedings of the American Association of Cancer Research*, 27:277 (Abstract 1099)(1986).
C. W. Taylor, et al., *Journal of Clinical Oncology*, 7:1733 (1989).
J. D. Hainsworth, et al., *Cancer Research*, 49:5217 (1989).
R. Levine, *Diabetes Care*, 7 (Suppl. 1):3-7 (1984).
G. F. Holland, et al., *Journal of Medicinal and Pharmaceutical Chemistry*, 3:99 (1961).
P. J. Houghton, et al., *Cancer Chemotherapy and Pharmacology*, 25:84 (1989).
P. J. Houghton, et al., *Cancer Research*, 50:318 (1990).
P. J. Houghton, et al., *Cancer Research*, 50:664 (1990).
P. J. Houghton, et al., *Biochemical Pharmacology*, 39:1187 (1990).
P. H. Dhahir, et al., In *Proceedings of the 36th ASMS Conference on Mass Spectroscopy and Allied Topics*, pp. 972-973 (1988).
G. F. Holland, *Journal of Organic Chemistry*, 26:1662 (1961).
*Chemical Abstracts*, 52:17180; citing Haack, et al., East German Patent 9688, Apr. 21, 1955.
F. Kurzer, *Chemical Reviews*, 50:1 (1952).
G. B. Grindey, et al., In *Proceedings of the American Association for Cancer Research*, 28:309 (Abstract 1224)(1987).
H. Breuer, et al., *Chimie Therapeutique*, Nov./Dec. 1973:659.
L. J. Lerner, et al., *Metabolism*, 14:578 (1965).
Taylor et al. "Clinical Pharmacology of a Novel Diarylsulfonylurea Anti-Cancer Agent" *J. of Clinical Oncology*, vol. 17, No. 11 (1989) pp. 1733-1740.

*Primary Examiner*—Richard L. Raymond
*Assistant Examiner*—P. O'Sullivan
*Attorney, Agent, or Firm*—Paul J. Gaylo; Leroy Whitaker; Joseph A. Jones

[57] ABSTRACT

This invention provides the use of certain indenesulfonamide derivatives in the treatment of susceptible neoplasms in mammals. Also provided are certain novel indenesulfonamide derivatives and their pharmaceutical formulations.

21 Claims, No Drawings

ANTITUMOR COMPOSITIONS AND METHODS OF TREATMENT

BACKGROUND OF THE INVENTION

In recent years fundamental advances have been made in the development of chemical agents and regimens of therapy to combat neoplastic diseases. Despite these continuing advances, cancers continue to exact intolerable levels of human pain and suffering. The need for new and better methods of treating neoplasms and leukemias continues to fuel efforts to create new classes of compounds, especially in the area of inoperable or metastatic solid tumors, such as the various forms of lung cancer. Of the one million new cases of cancer diagnosed in the United States each year, more than 90% represent non-hematopoetic tumors, where improvements in five-year survival rates have been modest, at best.

The recent avalanche of information regarding the basic biological processes involved in neoplasms has led to a deeper understanding of the heterogeneity of tumors. Ongoing work has led to the realization that individual tumors may contain many subpopulations of neoplastic cells that differ in crucial characteristics such as karyotype, morphology, immunogenicity, growth rate, capacity to metastasize, and response to antineoplastic agents.

It is because of this extreme heterogeneity among populations of neoplastic cells that new chemotherapeutic agents should have a wide spectrum of activity and a large therapeutic index. In addition, such agents must be chemically stable and compatible with other agents. It is also important that any chemotherapeutic regimen be as convenient and painless as possible to the patient.

This invention reports a series of sulfonylureas which are useful in the treatment of solid tumors. These compounds are orally active—which, of course, results in less trauma to the patient—and are relatively non-toxic. These compounds also have an excellent therapeutic index. The compounds and their formulations are novel.

Many sulfonylureas are known in the art. Certain of these compounds are known to have hypoglycemic activities, and have been used medicinally as such agents. In addition, sulfonylureas have been taught to have herbicidal and antimycotic activities. General reviews of compounds of this structural type are taught by Kurzer, *Chemical Reviews*, 50:1 (1952) and C. R. Kahn and Y. Shechter, *Goodman and Gilman's, The Pharmacological Basis of Therapeutics*, (Gilman, et al., 8th ed. 1990) 1484-1487. Some diarylsulfonylureas have been reported as being active antitumor agents. e.g., U.S. Pat. No. 4,845,128 of Harper, et al. (1989); European Patent Publication 0222475 (published May 20, 1987); European Patent Publication 0291269 (published Nov. 17, 1988); Grindey, et al., *American Association of Cancer Research*, 27:277 (1986); and Houghton et al., *Cancer Chemotherapy and Pharmacology*, 25:84-88 (1989). There is no suggestion in these references of the indenesulfonylureas of the instant application or that these compounds would be useful as antitumor agents.

Ongoing trials with the broad spectrum antineoplastic agent sulofenur [N-(indan-5-sulfonyl)-N'-(4-chlorophenyl)urea] have shown varying metabolic processes resulting in several major species and many minor species of metabolites. Initial preclinical pharmokinetic and disposition studies have been performed in mice, rats, dogs, and monkeys. These studies showed good adsorption and extensive metabolism of sulofenur in all species. The metabolic breakdown products of interest are as follows:

N-(1-hydroxyindan-5-sulfonyl)-N'-(4-chlorophenyl)urea;

N-(1-ketoindan-5-sulfonyl)-N'-(4-chlorophenyl)urea;

N-(3-hydroxyindan-5-sulfonyl)-N'(4-chlorophenyl)urea;

N-(3-ketoindan-5-sulfonyl)-N'-(4-chlorophenyl)urea;

N-(1,2-dihydroxyindan-5-sulfonyl)-N'-(4-chlorophenyl)urea;

Dihydroxyindanyl metabolite;

p-Chloroaniline;

2-Amino-5-chlorophenyl sulfate;

p-Chloro-oxanilic acid;

W. J. Ehlhardt, *Drug Metabolism and Disposition*, 19:370-375 (1991).

The main urinary metabolites of sulofenur in animal trials were identified as the mono-hydroxy- and mono-ketoindanyl metabolites. The 1-hydroxy- and 1-ketoindansulfonylureas were also found to be the major metabolites in patients receiving the drug in phase I clinical studies. P. H. Dhahir, et al., *Proceedings of the 36th ASMS Conference on Mass Spectroscopy and Allied Topics*, pp. 972-973 (1988); W. J. Ehlhardt, supra at 372.

Two of the metabolites, N-(1-hydroxyindan-5-sulfonyl)-N'-(4-chlorophenyl)urea and N-(1-ketoindan-5-sulfonyl)-N'-(4-chlorophenyl)urea, were found to be retained longer in humans than in the other species tested. As a means of minimizing the metabolic formation of these therapeutically inactive metabolites, which contribute to the adverse effects, the instant invention involves the synthesis and method of use of a series of indenesulfonylureas and formulations comprising the same. The formation of the double bond on the five-membered ring is designed to retard or inhibit the formation of the 1-ketoindanyl and 1-hydroxyindanyl metabolites.

SUMMARY OF THE INVENTION

This invention provides a method of treating susceptible neoplasms in mammals which comprises administering to a mammal in need of said treatment an effective amount of a compound of the Formula I.

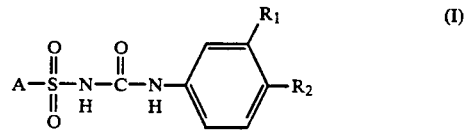

wherein:

A is

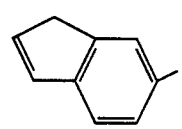

or

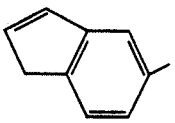

$R_1$ is halo or hydrogen; and $R_2$ is halo or trifluoromethyl; and pharmaceutically acceptable salts thereof.

This invention also provides novel compounds of the Formula I. Such compounds are especially preferred in the treatment of susceptible neoplasms in mammals.

In addition, this invention provides pharmaceutical formulations comprising a compound of Formula I, in combination with a suitable pharmaceutical carrier, diluent, or excipient. These formulations are useful in the treatment of mammals suffering from susceptible neoplasms.

In another embodiment, the present invention provides a method of treating susceptible neoplasms in mammals by administering to a mammal in need of said treatment an effective amount of at least one compound of Formula I.

DETAILED DESCRIPTION OF THE INVENTION AND PREFERRED EMBODIMENTS

As used herein, the term "halo" refers to fluoro, chloro, bromo, and iodo.

Preferred methods of use employ compounds of Formula I in which $R_1$ is chloro, fluoro, bromo, or hydrogen; and $R_2$ is chloro, fluoro, bromo, or trifluoromethyl.

Preferred compounds of the instant invention are those of Formula I in which $R_1$ is chloro, fluoro, bromo, or hydrogen; and $R_2$ is chloro, fluoro, bromo, or trifluoromethyl.

Illustrative compounds falling within the scope of this invention are:

N-[[(4-chlorophenyl)amino]carbonyl]-indene-6-sulfonamide;

N-[[(4-chlorophenyl)amino]carbonyl]-indene-5-sulfonamide;

N-[[(4-fluorophenyl)amino]carbonyl]-indene-6-sulfonamide;

N-[[(4-fluorophenyl)amino]carbonyl]-indene-5-sulfonamide;

N-[[(4-trifluoromethylphenyl)amino]carbonyl]-indene-6-sulfonamide;

N-[[(4-trifluoromethylphenyl)amino]carbonyl]-indene-5-sulfonamide;

N-[[(4-bromophenyl)amino]carbonyl]-indene-6-sulfonamide;

N-[[(4-bromophenyl)amino]carbonyl]-indene-5-sulfonamide;

N-[[(3,4-difluorophenyl)amino]carbonyl]-indene-6-sulfonamide;

N-[[(3,4-difluorophenyl)amino]carbonyl]-indene-5-sulfonamide;

N-[[3,4-dibromophenyl)amino]carbonyl]-indene-6-sulfonamide;

N-[[3,4-dibromophenyl)amino]carbonyl]-indene-5-sulfonamide;

N-[[(3,4-dichlorophenyl)amino]carbonyl]-indene-6-sulfonamide;

N-[[(3,4-dichlorophenyl)amino]carbonyl]-indene-5-sulfonamide;

N-[[3-chloro-4-fluorophenyl)amino]carbonyl]-indene-6-sulfonamide;

N-[[3-chloro-4-fluorophenyl)amino]carbonyl]-indene-5-sulfonamide;

N-[[(3-chloro-4-trifluoromethylphenyl)amino]carbonyl]-indene-6-sulfonamide;

N-[[(3-chloro-4-trifluoromethylphenyl)amino]carbonyl]-indene-5-sulfonamide;

N-[[(3-chloro-4-bromophenyl)amino]carbonyl]-indene-6-sulfonamide;

N-[[(3-chloro-4-bromophenyl)amino]carbonyl]-indene-5-sulfonamide;

N-[[(3-fluoro-4-chlorophenyl)amino]carbonyl]-indene-6-sulfonamide;

N-[[(3-fluoro-4-chlorophenyl)amino]carbonyl]-indene-5-sulfonamide;

N-[[(3-fluoro-4-bromophenyl)amino]carbonyl]-indene-6-sulfonamide;

N-[[(3-fluoro-4-bromophenyl)amino]carbonyl]-indene-5-sulfonamide;

N-[[(3-fluoro-4-trifluoromethylphenyl)amino]carbonyl]-indene-6-sulfonamide;

N-[[(3-fluoro-4-trifluoromethylphenyl)amino]carbonyl]-indene-5-sulfonamide;

N-[[(3-bromo-4-chlorophenyl)amino]carbonyl]-indene-6-sulfonamide;

N-[[(3-bromo-4-chlorophenyl)amino]carbonyl]-indene-5-sulfonamide;

N-[[(3-bromo-4-fluorophenyl)amino]carbonyl]-indene-6-sulfonamide;

N-[[(3-bromo-4-fluorophenyl)amino]carbonyl]-indene-5-sulfonamide;

N-[[(3-bromo-4-trifluoromethylphenyl)amino]carbonyl]-indene-6-sulfonamide;

N-[[(3-bromo-4-trifluoromethylphenyl)amino]carbonyl]-indene-5-sulfonamide.

The compounds of Formula I are generally referred to as derivatives of N-[[(substituted phenyl)amino]carbonyl]indenesulfonamides. Alternatively, the compounds can be referred to as 1- and 3-substituted sulfonylureas or N- and N'-substituted sulfonylureas.

This invention includes the pharmaceutically acceptable salts of the compounds of Formula I. The compounds of this invention can react with basic materials such as alkali metal- or alkaline earth metal hydroxides, carbonates, and bicarbonates including, without limitation, sodium hydroxide, sodium carbonate, potassium hydroxide, calcium hydroxide, lithium hydroxide, etc. to form pharmaceutically acceptable salts such as the corresponding sodium, potassium, lithium, or calcium salt. Nontoxic organic bases can also be used, including primary, secondary, and tertiary alkyl amines such as methylamine, triethylamine, and the like.

The compounds of Formula I can be prepared by any of the methods known in the literature. Generally, these methods involve either the reaction of a sulfonamide with an isocyanate or a reaction of a sulfonylcarbamate with an appropriately-substituted aniline.

The preferred method of preparing the compound of Formula I is that of the reaction of an arylisocyanate of the Formula II

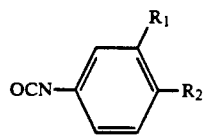

with a sulfonamide of the Formula III

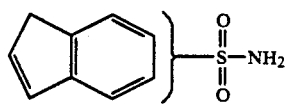

where $R_1$ and $R_2$ are the same as previously defined, in the presence of an acid scavenger such as sodium hydroxide, potassium hydroxide, lithium hydroxide, sodium methoxide, sodium hydride and the like.

The reaction between compounds II and III is usually performed using equimolar amounts of the two reactants, although other ratios are operative. The reaction is preferably carried out in a solvent which is nonreactive under the reaction conditions such as benzene, toulene, acetonitrile, ethyl ether, tetrahydrofuran, dioxane, or most preferably acetone, generally in an acetone/water mixture.

The reaction can be carried out at temperatures from about 0° C. to about 100 ° C. At the preferred temperature range of about 20° C. to about 30° C., the reaction produces an exotherm and the reaction is usually complete within one hour. The product thus obtained is recovered by neutralization followed by filtration, and can be purified, if desired, by any number of methods known to those skilled in the art, such as chromatography or crystallization.

The sulfonamide of Formula III can be prepared by one of several methods depending upon the starting materials used. For example, the preferred method of preparing the indene-6-sulfonamide is the reaction of 1-hydroxy-5-indanesulfonamide with p-toluenesulfonic acid. The 1-hydroxy-5-indanesulfonamide and the 1-keto-5-indanesulfonamide are prepared by methods well-known in the art. See, e.g., J. Howbert and T. Crowell, *Synthetic Communications*, 20:3193-3200 (1990) and the references cited therein.

The starting materials and intermediates for the preparation of the present compounds are commercially available or can be readily prepared by the above-described methods or other methods known in the literature.

The terms and abbreviations used in the instant examples have their normal meanings unless otherwise designated. For example, "°C." refers to degrees Celsius; "N" refers to normal or normality; "mmole" means millimole; "g" refers to gram; "mL" means milliliter; "M" refers to molar or molarity; and "NMR" refers to nuclear magnetic resonance.

The following examples further illustrate the preparation of the compounds of this invention. The examples are illustrative only and are not intended to limit the scope of the invention in any way.

Preparation 1

1-Hydroxy-5-indanesulfonamide

To a stirred solution of 1-keto-5-indanesulfonamide (6.3 g, 30 mmol), in 120 mL of 50% aqueous methanol at 0° C. was added $NaBH_4$ (1.1 g, 30 mmol) in several portions. The cooling bath was removed and the mixture allowed to stir at room temperature for 30 minutes. After removal of the methanol in vacuo, the residue was extracted with ethyl acetate (4×75 mL) and the combined organic phase dried ($Na_2SO_4$). Filtration, followed by evaporation of the solvent, gave 5.4 g (84%) of product as a white solid.

Analysis of the product gave the following results: mp=144°-145° C.; $R_f$(EtOAc)=0.43; $^1$H NMR (300 MHz, $d_6$-DMSO) δ 1.76 (m, 1H, $CH_2$), 2.35 (m, 1 H, $CH_2$), 2.77 (m, 1H, $CH_2$), 2.94 (m, 1H, $CH_2$), 5.05 (bd, 1H, J=4.9 Hz, CH), 5.40 (bd, 1H, J=5 Hz, exchanges with $D_2O$, OH), 7.24 (bs, 2H, exchanges with $D_2O$, $SO_2NH_2$), 7.44 (d, 1H, J=8.5 Hz, Ar-H), 7.63 (s overlapping d, 2H, Ar-H),; IR(KBr) 3476, 3321, 3174, 3084, 1570, 1409, 1332, 1311, 1166, 1137, 1062, 922 and 826 $cm^{-1}$; UV(EtOH) λmax(ε) 278.4 (1356), 270.4 (1418), 228.2 (10198) and 204.0 (22287) nm; FDMS (MeOH) m/e 213 (M+).

Analysis for $C_9H_{11}NO_3S$:
Theory: C, 50.69; H, 5.20; N, 6.57.
Found: C, 50.91; H, 5.17; N, 6.45.

Preparation 2

Indene-6-sulfonamide

A mixture of the product of Example 1 (3.07 g, 14.5 mmol) and p-toluenesulfonic acid monohydrate (276 mg, 1.5 mmol) in 200 mL 1,2-dichloroethane was heated at reflux for 1 hour. After cooling, the solution was washed with 5% $NaHCO_3$ (1×100 mL) and water (1×100 mL) and dried ($Na_2SO_4$). Concentration in vacuo gave a yellow solid which was chromatographed on silica gel (20-40% EtOAc/hexane) to give 1.9 g (65%) of the product as a white solid.

Analysis of the product gave the following results: mp=155°-156° C.; $R_f$(EtOAc)=0.61; $^1$H NMR (300 MHz, $d_6$-DMSO) δ 3.51 (s, 2H, $CH_2$), 6.83 (d, 1H, J=5.5 Hz, CH), 7.00 (d, 1H, J=5.5 Hz, CH), 7.25 (bs, 2H, exchanges with $D_2O$, $SO_2NH_2$), 7.55 (d, 1H, J=8.0 Hz, Ar-H), 7.72 (d, 1H, J=8.0 Hz, Ar-H), 7.91 (s, 1H, Ar-H); $^{13}$C NMR (75 MHz, $d_6$-DMSO) δ 39.5, 121.2, 121.4, 124.7, 131.6, 139.1, 140.8, 144.2 and 148.2; IR(KBr) 3320, 3238, 2903, 2890, 1604, 1390, 1325, 1181, 1149, 1129, 1066, 866, 817 and 585 $cm^{-1}$; UV(EtOH) λmax(ε) 261.4 (16629) and 206.0 (17811) nm; FDMS (MeOH) m/e 195 (M+).

Analysis for $C_9H_9NO_2S$: Theory: C, 55.37; H, 4.65; N, 7.17. Found: C, 55.66; H, 4.77; N, 7.12.

Example 1

N-[[(4-chlorophenyl)amino]carbonyl]-indene-5-sulfonamide (A) and N-[[(4-chlorophenyl)amino]carbonyl]-indene-6-sulfonamide (B)

A solution of the product of Example 2 (2.1 g, 10.8 mmol) in acetone (5 mL) and 1N aqueous NaOH (10.8 mL, 10.8 mmol) was treated dropwise with a solution of p-chlorophenylisocyanate (2.0 g, 12.8 mmol) in 5 mL acetone over 20 minutes. After stirring 2 hours, the insoluble bis(p-chlorophenyl)urea was removed by filtration and the resulting clear solution neutralized by the addition of 1N aqueous HCl (10.8 mL, 10.8 mmol). The slurry was stirred 30 minutes, filtered and washed with $H_2O$ (100 mL) and ether (50 mL). Drying gave 3.4 g of solid, which was suspended in 100 mL of $H_2O$ and treated with 1N aqueous NaOH (20 mL). The insoluble material was removed by filtration through a pad of Celite. Neutralization of the filtrate with 20 mL of 1N aqueous HCl precipitated a solid which was collected by filtration and dried to yield 2.21 g (59%) of the product. NMR studies indicated the product to be a 7:5 mixture of the 6- and 5-indenylsulfonyl isomers. These isomers may be separated, if desired, by techniques which are well known in the art.

Analysis of the product mixture gave the following results: mp=159°-161° C.; $R_f$ (1/9 MeOH/CHCl$_3$)=0.36; $^1$H NMR (300 MHz, d$_6$-DMSO): A: δ 3.55 (s, 2 H, C$\underline{H}_2$), 6.90 (d, 1H, J=5.6 Hz, C$\underline{H}$), 7.05 (m, 1H, C$\underline{H}$), 7.25-7.35 (m, 4H, Ar-$\underline{H}$), 7.60 (d, 1H, J=8.0 Hz, Ar-$\underline{H}$), 7.84 (d, 1 H, J=8.0 Hz, Ar-$\underline{H}$), 8.02 (s, 1H, Ar-$\underline{H}$), 8.96 (bs, 1 H, exchanges with D$_2$O, N$\underline{H}$), 10.82 (bs, 1$\underline{H}$, exchanges with D$_2$O, N$\underline{H}$); B δ 3.52 (s, 2H, C$\underline{H}_2$), 6.78 (d, 1H, J=5.6 Hz, C$\underline{H}$), 7.05 (m, 1H, C$\underline{H}$), 7.25-7.35 (m, 4 H, Ar-$\underline{H}$), 7.70 (d, 1H, J=8.0 Hz, Ar-$\underline{H}$), 7.78 (d, 1H, J=8.0 Hz, Ar-$\underline{H}$), 7.98 (s, 1H, Ar-$\underline{H}$), 8.95 (bs, 1H, exchanges with D$_2$O, N$\underline{H}$), 10.82 (bs, 1H, exchanges with D$_2$O, N$\underline{H}$); IR(KBr) 3367, 3274, 1716, 1606, 1545, 1498, 1464, 1341, 1148, 1033, 922, 696 and 587 cm$^{-1}$; UV(EtOH) λmax(ε) 251.8 (29988) and 204.8 (37094) nm; FDMS (MeOH) m/e 348, 350 (M+).

Analysis for $C_{16}H_{13}ClN_2O_3S$: Theory: C, 55.09; H, 3.76; N, 8.03. Found: C, 55.19; H, 3.72; N, 7.84.

The compounds of Formula I have been shown to be active against transplanted mouse tumors in vivo. The compounds were tested in C3H mice bearing a 6C3HED lymphosarcoma, also known as the Gardner lymphosarcoma (GLS). The 6C3HED lymphosarcoma was obtained from the Division of Cancer Treatment, National Cancer Institute, Tumor Bank, maintained at E. G. and G. Mason Research (Worcester, Mass.). First passage tumor was stored in liquid nitrogen using standard techniques. The transplanted tumor was reestablished from the Tumor Bank every six months or as needed. The tumor was maintained by serial passage twice weekly in C3H mice.

In the procedures utilized here, the tumor was removed from passage animals and minced into 1- to 3-mm cubic fragments using sterile techniques. Tumor pieces were checked for sterility using both Antibiotic Medium 1 and Brain Heart Infusion (Difco, Detroit, Mich.). Recipient mice were shaved and the tumor pieces were implanted subcutaneously in an axillary site by trochar.

Drug therapy on the appropriate schedule was initiated on the day after tumor implantation. The compound being tested was mixed with 2.5% Emulphor EL620 from GAF Corporation (1:40 dilution in 0.9% saline). The total dosage volume for each administration was 2.5 mL. All animals were weighed at the beginning and end of administration of the subject compounds. Food and water were provided ad libitum.

Each control group and each dosage level of the treated groups consisted of 10 mice selected at random from the pool of implanted animals. The compounds were administered orally by gavage with the use of an 18-gauge needle. Compounds were dosed daily for 8 days.

The tumor was measured the day after treatment ended with two dimensional measurements (width and length) of the tumor taken using Vernier calipers. Tumor weights were calculated from these measurements using the following formula:

Tumor weight (mg)=[tumor length (mm)×[tumor width (mm)]$^2$]÷2

At least one control group of an equal number of mice was treated with the same volume of 2.5% Emulphor only. The percent inhibition is determined by subtracting the ratio of the mean tumor size of the test group relative to the control group from one and multiplying the result by 100.

The results of several experiments in mice bearing a 6C3HED lymphosarcoma when the instant compounds were administered orally are provided in Table I. In the Table, column 1 gives the dose level of the compound mixture of Example 1, column 2 provides the percent inhibition of tumor growth, and column 3 gives the number of mice which died relative to the total number of animals in the group.

TABLE 1

| Dosage | Percent Inhibition | Toxic/Total |
|---|---|---|
| 25.0 | 16 | 0/10 |
| 50.0 | 36 | 0/10 |
| 100.0 | 77 | 0/10 |
| 150.0 | 100 | 0/10 |
| 300.0 | 100 | 0/10 |

The compounds of Formula I are antineoplastic agents and the invention provides a method of treating susceptible neoplasms. In particular, the present compounds are useful in treating solid tumors including carcinomas such as ovarian, non-small cell lung, gastric, pancreatic, prostate, renal cell, breast, colorectal, small cell lung, melanoma, and head and neck; and sarcomas such as Kaposi's sarcoma and rhabdomyosarcoma.

The instant compounds can be administered individually or in combination, preferably orally, and usually in the form of a pharmaceutical composition. Such compositions are prepared in a manner well known in the pharmaceutical art and comprise at least one active compound. Accordingly, the present invention also includes pharmaceutical compositions which contain, as the active ingredient, certain compounds of Formula I associated with a pharmaceutically acceptable carrier. The invention further comprises the method of treating susceptible neoplasms using compositions containing as an active ingredient at least one compound of Formula I.

In making the compositions of the present invention, as well as compositions containing other compounds of Formula I, the active ingredients are usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compounds are effective over a wide dosage range. For examples, dosages per day normally fall within the range of about 0.5 to about 1200 mg/kg of body weight. In the treatment of adult humans, the range of about 1 to about 50 mg/kg, in single or divided dose, is preferred. However, it will be understood that the amount of the compound actually administered will be determined by a physician, in the light of the relevant circumstances, including the condition to be treated, the choice of compound to be administered, the chosen route of administration, the age, weight, and response of the individual patient, and the severity of the patient's symptoms, and therefore the above dosage ranges are not intended to limit the scope of the invention in any way.

Formulation 1

Hard gelatin capsules are prepared using the following ingredients:

| | |
|---|---|
| N-[[(4-fluorophenyl)amino]carbonyl]-indene-6-sulfonamide | 250.0 |
| Starch | 305.0 |
| Magnesium stearate | 5.0 |

The above ingredients are mixed and filled into hard gelatin capsules in 560 mg quantities.

Formulation 2

A tablet formula is prepared using the ingredients below:

| | Quantity (mg/tablet) |
|---|---|
| N-[[(4-fluorophenyl)amino]carbonyl]-indene-5-sulfonamide | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

| | Weight % |
|---|---|
| N-[[(4-trifluoromethylphenyl)amino]-carbonyl]-indene-6-sulfonamide | 5 |
| Lactose | 95 |

The active mixture is mixed with the lactose and the mixture is added to a dry powder inhaling appliance.

Formulation 4

Tablets, each containing 60 mg of active ingredient, are prepared as follows:

| | |
|---|---|
| N-[[(4-trifluoromethylphenyl)amino]-carbonyl]-indene-5-sulfonamide | 60.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5

Capsules, each containing 80 mg of medicament are made as follows:

| | |
|---|---|
| N-[[(3,4-difluorophenyl)amino]-carbonyl]-indene-6-sulfonamide | 80.0 mg |
| Starch | 109.0 mg |
| Magnesium stearate | 1.0 mg |
| Total | 190.0 mg |

The active ingredient, cellulose, starch, and magnesium stearate are blended, passed through a No. 20 mesh U.S. sieve, and filled into hard gelatin capsules in 190 mg quantities.

Formulation 6

Suppositories, each containing 225 mg of active ingredient are made as follows:

| | |
|---|---|
| N-[[(3,4-difluorophenyl)amino-carbonyl]-indene-5-sulfonamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of medicament per 5.0 mL dose are made as follows:

| | |
|---|---|
| N-[[(3,4-dichlorophenyl)amino]-carbonyl]-indene-5-sulfonamide | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor | q.v. |
| Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of medicament, are made as follows:

| | |
|---|---|
| N-[[(3-chloro-4-fluorophenyl)amino]-carbonyl]-indene-6-sulfonamide | 150.0 mg |
| Starch | 407.0 mg |
| Magnesium stearate | 3.0 mg |
| Total | 560.0 mg |

The active ingredient, cellulose, starch, and magnesium stearate are blended, passed through a No. 20 mesh U.S. sieve, and filled into hard gelatin capsules in 560 mg quantities.

We claim:

1. A compound of the formula

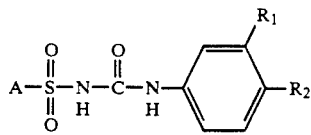

wherein:
A is

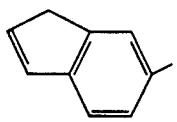

or

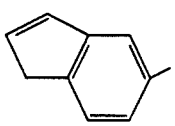

$R_1$ is halo or hydrogen; and
$R_2$ is halo or trifluoromethyl,
and pharmaceutically acceptable salts thereof.

2. A compound according to claim 1 wherein $R_2$ is halo.

3. A compound according to claim 1 wherein $R_1$ is hydrogen.

4. A compound according to claim 3 wherein the compound is N-[[(4-chlorophenyl)amino]carbonyl]-indene-5-sulfonamide.

5. A compound according to claim 3 which is N-[[(4-chlorophenyl) amino]carbonyl]-indene-6-sulfonamide.

6. A compound according to claim 2 which is N-(3,4-dichlorophenyl)amino]carbonyl]-indene-5-sulfonamide.

7. A compound according to claim 2 which is N-[[(3,4-dichlorophenyl)amino]carbonyl]-indene-6-sulfonamide.

8. A method of treating susceptible neoplasms in mammals which comprises administering to a mammal in need of said treatment an effective amount for treating susceptible neoplasms of a compound of the formula $$A-\overset{\overset{O}{\|}}{\underset{\underset{O}{\|}}{S}}-\overset{}{\underset{H}{N}}-\overset{\overset{O}{\|}}{C}-\overset{}{\underset{H}{N}}-\text{phenyl}(R_1, R_2)$$

wherein:
A is or $R_1$ is halo or hydrogen; and
$R_2$ is halo or trifluoromethyl,
and pharmaceutically acceptable salts thereof.

9. A method of claim 8 employing a compound wherein $R_2$ is halo.

10. A method of claim 9 employing a compound wherein $R_1$ is hydrogen.

11. A method of claim 10 employing N-[[(4-chlorophenyl)amino] carbonyl]-indene-5-sulfonamide.

12. A method of claim 10 employing N-[[(4-chlorophenyl)amino] carbonyl]-indene-6-sulfonamide.

13. A method of claim 9 employing N-[[(3,4-dichlorophenyl) amino]carbonyl]-indene-5-sulfonamide.

14. A method of claim 9 employing N-[[(3,4-dichlorophenyl) amino]carbonyl]-indene-6-sulfonamide.

15. A pharmaceutical formulation comprising an effective amount of a compound of the formula wherein:

A is

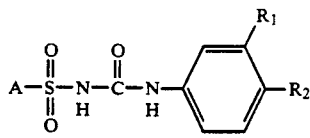

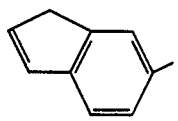

or

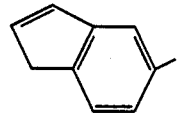

$R_1$ is halo or hydrogen; and
$R_2$ is halo or trifluoromethyl;
and pharmaceutically acceptable salts thereof, in combination with a suitable pharmaceutical excipient.

16. A formulation according to claim 15 employing a compound wherein $R_2$ is halo.

17. A formulation according to claim 16 employing a compound wherein $R_1$ is hydrogen.

18. A formulation according to claim 17 employing N-[[(4-chlorophenyl)amino]carbonyl]-indene-6-sulfonamide.

19. A formulation according to claim 17 employing N-[[(4-chlorophenyl)amino]carbonyl]-indene-5-sulfonamide.

20. A formulation according to claim 16 employing N-[[(3,4-dichlorophenyl)amino]carbonyl]-indene-5-sulfonamide.

21. A formulation according to claim 16 employing N-[[(3,4-dichlorophenyl)amino]carbonyl]-indene-6-sulfonamide.

* * * * *